United States Patent [19]

Mori et al.

[11] Patent Number: 5,288,682
[45] Date of Patent: Feb. 22, 1994

[54] CATALYST FOR ASYMMETRIC INDUCTION

[75] Inventors: Atsunori Mori; Shohei Inoue, both of Tokyo, Japan

[73] Assignee: Sumitomo Chemical Co., Ltd., Osaka, Japan

[21] Appl. No.: 851,285

[22] Filed: Mar. 12, 1992

[30] Foreign Application Priority Data

Mar. 12, 1991 [JP] Japan .................................. 3-046482

[51] Int. Cl.$^5$ .............................................. B01J 31/00
[52] U.S. Cl. ...................................... 502/167; 502/171
[58] Field of Search ................................ 502/167, 171

[56] References Cited

U.S. PATENT DOCUMENTS 5,118,665  6/1992  Pickart ................................ 514/6

FOREIGN PATENT DOCUMENTS 0109681  5/1984  European Pat. Off. .
0271868  6/1988  European Pat. Off. .

OTHER PUBLICATIONS

Chemical Abstracts, vol. 115, No. 23, Dec. 9, 1991, Columbus, Ohio, US; abstract No. 255754j, A. Mori et al: 'Peptide-metal complex as an asymmetric catalyst . . . ' p. 820; col. 2; abstract & Tetrahedron Lett. vol. 32, No. 34, 1991, pp. 4333–4336.
Chemical Abstracts, vol. 97, No. 5, Aug. 2, 1982, Columbus, Ohio, US; abstract No. 39355x, J. Oku et al; 'Asymmetric cyanohydrin synthesis catalyzed by synthestic dipeptides' p. 618; col. 2; abstract & Makromol. Chem. vol. 183, No. 3, 1982, pp. 579–586.
J. Org. Chem., 1990, 55, 181–185.
J. Chem. Soc. Chem. Commun., 1990, 1364–1365.
J. Am. Chem. Soc., 1962, 84, 2417–2420.

Primary Examiner—Patrick P. Garvin
Assistant Examiner—Brent M. Peebles
Attorney, Agent, or Firm—Sughrue, Mion, Zinn, Macpeak & Seas

[57] ABSTRACT

Optically active cyanohydrins are prepared by addition of hydrogen cyanide to aldehydes in the presence of catalysts which comprise the dipeptide derivative represented by the formula wherein $R^1$ represents an isopropyl group, an isobutyl group, a sec-butyl group, a tert-butyl group, a methyl group, a benzyl group or a phenyl group, $R^2$ represents a benzyl group, an indol-3-ylmethyl group, an isopropyl group, an isobutyl group or a phenyl group, $R^3$ represents a lower alkoxy group, a hydroxy group or a mono- or di-lower alkylamino group, $R^4$ represents a hydrogen atom, or $R^2$ and $R^4$ are bonded together at their terminals to form a $CH_2CH_2CH_2$ group, $R^5$, $R^6$, $R^7$ and $R^8$ are the same or different, and each represents a hydrogen atom, a halogen atom, a lower alkyl group or a lower alkoxy group or $R^5$ and $R^6$, $R^6$ and $R^7$, or $R^7$ and $R^8$ are bonded together at their terminals to form $CH=CH-CH=CH$ or $OCH_2O$, and * denotes an absolute configuration of S or R, and a titanium (IV) alkoxide.

12 Claims, No Drawings

CATALYST FOR ASYMMETRIC INDUCTION

The present invention relates to a catalyst for asymmetric induction. More particularly, it relates to catalysts useful for preparation of optically active cyanohydrins by addition of hydrogen cyanide to aldehydes.

The present inventors have previously reported that (R)-cyanohydrin isomers are obtained by asymmetric addition reaction of hydrogen cyanide to aldehydes with cyclo-[(S)-phenyl-alanyl-(S)-histidyl] [Inoue et al., J. Chem. Soc., Chem. Comm., 229 (1981): Bull, Chem. Soc. Jpn., 59, 893 (1986)]. For example, (R)-mandelonitrile is obtained at a relatively high purity and in a high yield by allowing benzaldehyde to react with hydrogen cyanide in the presence of cyclo-[(S)-phenylalanyl-(S)-histidyl) ].

The present inventors have found a further excellent catalyst for asymmetric induction in the course of researches on asymmetric induction catalyzed by dipeptide derivatives. Thus, the present invention has been accomplished.

That is, the present invention is to provide a catalyst for asymmetric induction comprising dipeptide derivatives represented by the formula

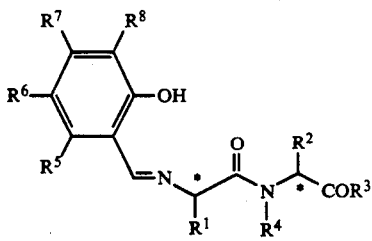
[I]

wherein $R^1$ represents an isopropyl group, an isobutyl group, a sec-butyl group, a tert-butyl group, a methyl group, a benzyl group or a phenyl group, $R^2$ represents a benzyl group, an indol-3-ylmethyl group, an isopropyl group, an isobutyl group or a phenyl group, $R^3$ represents a lower alkoxy (e.g. $C_{1-4}$ alkoxy such as methoxy, ethoxy) group, a hydroxyl group or a mono- or di-lower alkylamino (e.g. $C_{1-4}$ alkyl such as methyl, ethyl) group, $R^4$ represents a hydrogen atom, or $R^2$ and $R^4$ are bonded together at their terminals to form a $CH_2CH_2CH_2$ group, $R^5$, $R^6$, $R^7$ and $R^8$ are the same or different, and each represents a hydrogen atom, a halogen atom (e.g., a fluorine atom, a chlorine atom, a bromine atom), a lower alkyl (e.g., $C_{1-4}$ alkyl such as methyl, ethyl, propyl, isopropyl, butyl, isobutyl, sec-butyl, tert-butyl) group or a lower alkoxy (e.g., $C_{1-4}$ alkoxy such as methoxy, ethoxy) group, or $R^5$ and $R^6$, $R^6$ and $R^7$ or $R^7$ and $R^8$ are bonded together at their terminals to form $CH=CH-CH=CH$ or $OCH_2O$ and * denotes an absolute configuration of S or R, and titanium (IV) alkoxides. It is further to provide a process for preparing an optically active cyanohydrin by addition of hydrogen cyanide to an aldehyde in the presence of the aforementioned catalyst.

Several embodiments of the dipeptide derivatives represented by the formula [I] are given below

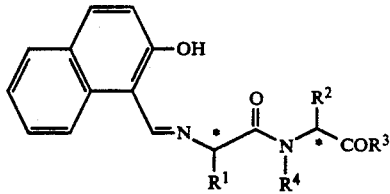
[II]

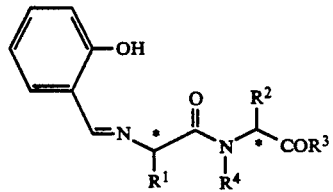

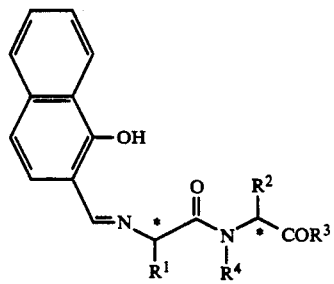

wherein R, $R^2$, $R^3$, $R^4$, and * are the same as those defined above. In the dipeptide derivative represented by the formula [I] used for the catalyst of the present invention; as the $R^1$ substituent an isopropyl group, an isobutyl group, a sec-butyl group, a tert-butyl group, a methyl group or a benzyl group is preferred; and as the $R^2$ substituent a benzyl group, an indol-3-ylmethyl group, an isopropyl group or an isobutyl group is preferred; and as the $R^3$ substituent a lower alkoxy group is preferred; and as the $R^4$ substituent a hydrogen atom is preferred; and not less than 2 substituents of $R^5$, $R^6$, $R^7$ and $R^8$ are preferably hydrogen atoms.

The dipeptide derivative represented by the formula [I] used for the catalyst of present invention can be prepared, for example, by condensation of a salicyl aldehyde derivative such as 2-hydroxy-1-naphthaldehyde and dipeptides as shown in the following scheme.

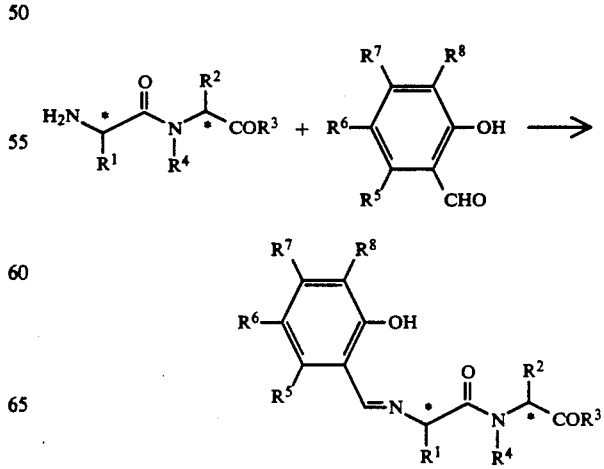

wherein $R^1$, $R^2$, $R^3$, $R^4$, $R^5$, $R^6$, $R^7$, $R^8$ are * are the same as those defined above.

The dipeptides used for the condensation with the salicyl aldehyde derivative such as 2-hydroxy-1-naphthaldehyde can be prepared according to any of the conventional methods for synthesizing peptides. For example, by the condensation of N-benzyloxycarbonyl-(S)-valine, N-benzyloxycarbonyl-(S)-leucine, N-benzyloxycarbonyl-(S)-isoleucine, N-benzyloxycarbonyl-(S)-tert-leucine, N-benzyloxy-carbonyl-(S)-alanine, N-benzyloxycarbonyl-(S)-phenylalanine or the corresponding R-isomers thereof with (S)-phenylalanine alkyl esters or amides such as lower alkyl esters having 1-4 carbon atoms (e.g. a methyl ester, an ethyl ester or the like) or mono- or di-lower alkylamides (e.g. butylamide. diethylamide or the like), or (S)-tryptophan alkyl esters or amides or R-isomers thereof in the presence of isobutyl chloroformate by the mixed acid anhydride method, the corresponding dipeptide derivatives such as N-benzyloxycarbonyl-(S)-valyl-(S)-phenylalanine methyl ester can be obtained. The dipeptide derivatives are then subjected to hydrogenolysis in the presence of palladium/carbon and condensation with the salicyl aldehyde derivative such as 2-hydroxy-1-naphthaldehyde.

The titanium (IV) alkoxides used as a component of the catalyst are lower alkoxides (e.g. $C_{1-4}$ alkoxides such as ethoxide, isopropoxide, propoxide, butoxide) of titanium (IV) such as titanium (IV) tetraethoxide, titanium (IV) tetraisopropoxide, titanium (IV) tetrapropoxide, titanium (IV) tetrabutoxide or the like. The titanium alkoxides are usually used in a molar ratio of ca. 0.5-2, preferably 1-2 to the compound represented by the formula [I].

It is presumed that the catalyst of the present invention is a complex consisting of the dipeptide derivatives and the titanium (IV) alkoxides, although the stereochemistry of the catalyst has not yet been established.

The catalyst obtained in the above is very useful as a catalyst for preparing optically active cyanohydrins by addition of hydrogen cyanide to aldehyde. For example, when a dipeptide derivative, Nap—S—Val—S—Phe—OMe, which is the compound represented by the formula [II]; $R^1$, an isopropyl group; $R^2$, a benzyl group; $R^3$, a methoxy group; $R^4$, a hydrogen atom; all of the absolute configurations thereof being S-isomers, and titanium (IV) tetraethoxide are used as the component of the catalyst of the present invention, (R)-mandelonitrile is produced by a reaction of benzaldehyde and hydrogen cyanide in the presence of the catalyst. On the other hand, when a dipeptide derivative, Nap—R—Val—R—Phe—OMe, which is the compound represented by the formula [II]; $R^1$, an isopropyl group; $R^2$, a benzyl group; $R^3$, a methoxy group; $R^4$, hydrogen atom; all of the absolute configurations thereof being R-isomers, and titanium (IV) tetraethoxide are used, (S)-mandelonitrile is produced. Thus, the catalyst of the present invention can be used as a catalyst for preparing a variety of optically active cyanohydrins which are useful as intermediates in the preparation of pharmaceuticals, agrochemicals such as pyrethroid insecticides, perfumes or the like.

In the catalyst of the present invention, each amino acid component of the dipeptide derivative represented by the formula [I] preferably has the same configuration, in other words, both absolute configurations relating to the carbon atoms represented by * are S- or R-isomers from the viewpoint of optical yield of the reaction.

Substrate compounds to which the catalyst of the present invention works are, in addition to the aforementioned benzaldehyde, aromatic aldehydes such as p-methylbenzaldehyde, m-methoxybenzaldehyde, naphthaldehyde, m-phenoxybenzaldehyde optionally substituted by one to two halogen atoms (e.g., a fluorine atom, a chlorine atom, a bromine atom), furfural or the like, aliphatic aldehydes such as heptanal or the like, or alicyclic aldehydes such as cyclohexanecarboaldehyde or the like.

When the catalyst of the present invention is used for the asymmetric synthesis of optically active cyanohydrins, such amount of 1-15% by mole to the aldehyde is enough. The synthesis is usually conducted by allowing an aldehyde to react with hydrogen cyanide whose amount is 1-5 moles to the aldehyde, in an inert solvent such as toluene, methylene chloride, ethyl ether, isopropyl ether or the like, at a temperature in the range from $-80°$ C. to room temperature, preferably from $-50°$ C. to room temperature. After the termination of reaction, the reaction mixture is poured into a dilute hydrochloric acid-methanol solution. After excess hydrogen cyanide is removed under reduced pressure, the solution is subjected to the usual after-treatments to give a desired optically active cyanohydrin.

EXAMPLES

The present invention is further explained with reference to Examples.

EXAMPLE 1

Nap—S—Val—S—Trp—OMe, which is the compound represented by the formula [II]; $R^1$, an isopropyl group; $R^2$, an indol-3-ylmethyl group; $R^3$, a methoxy group; $R^4$, a hydrogen atom; all of the absolute configurations thereof being S-isomers (0.05 mmole) was suspended in 3 ml of toluene at room temperature under an argon atmosphere, and titanium (IV) tetraethoxide (0.05 mmole) was added to the suspension under the same atmosphere as above. After being stirred for 30 minutes, the reaction mixture was cooled to $-78°$ C., and benzaldehyde (0.5 mmole) and hydrogen cyanide (0.75 mmole) were added. The mixture was further stirred at $-40°$ C. for 3 hours, and the reaction mixture was poured into a dilute hydrochloric acid-methanol solution. The excessive amount of hydrogen cyanide was removed under reduced pressure, and the mandelonitrile was recovered from the organic layer in 85% yield. The product contained the R- and S-isomers at a ratio of 94:6. The yield was calculated from integrating intensities of the $^1$H—NMR spectrum, and the ratio of the R-and S-isomers was determined by the integrating intensities of the signals corresponding to the methyne protons on the hu 1H—NMR spectrum after the product was converted to the corresponding menthyl carbonate according to the usual method. [Tanaka et al., J. Org. Chem., 55, 181 (1990); Mori et al., Chem. Lett., 1989, 2119].

EXAMPLE 2

The procedure was conducted in the same manner as in Example 1 except that titanium (IV) tetraisopropoxide (0.05 mmole) was used in place of the titanium (IV) tetraethoxide (0.05 mmole) and that the stirring was continued at $-20°$ C. for 2.5 hours in place of $-40°$ C. for 3 hours, to give mandelonitrile. Yield: 96%. The product contained the R- and S-isomers at a ratio of 89:11.

EXAMPLE 3

The procedure was conducted in the same manner as in Example 1 except that Nap—S—Val—S—Phe—OMe was used in place of the Nap—S—Val—S—Trp—OMe and that the stirring was continued at −40° C. for 4 hours in place of −40° C. for 3 hours, to give mandelonitrile. Yield: 85%. The product contained the R- and S-isomers at a ratio of 93:7.

EXAMPLE 4

The procedure was conducted in the same manner as in Example 3 except that Nap—S—Val—S—Phe—OMe was used in place of the Nap—S—Val—S—Phe—OMe, to give mandelonitrile. Yield: 85%. The product contained the R- and S-isomers at a ratio of 9:91.

EXAMPLE 5

The procedure was conducted in the same manner as in Example 2 except that Nap—R—Val—S—Phe—OMe was used in place of the Nap—S—Val—S—Trp—OMe and that the stirring was continued at −20° C. for 4 hours in place of −20° C. for 2.5 hours, to give mandelonitrile. Yield: 84%. The product contained the R- and S-isomers at a ratio of 31:69.

EXAMPLE 6

The procedure was conducted in the same manner as in Example 1 except that 2-naphthaldehyde was used in place of the benzaldehyde, and that the stirring was continued at −40° C. for 7.5 hours in place of −40° C. for 3 hours, to give α-hydroxy-(2-naphthyl)-acetonitrile. Yield: 88%. The product contained the R- and S-isomers at a ratio of 95:5.

EXAMPLE 7

The procedure was conducted in the same manner as in Example 6 except that furfural was used in place of the 2-naphthaldehyde, to give α-hydroxy-furfurylnitrile. Yield: 74%. The product contained the R- and S-isomers at a ratio of 7:93.

EXAMPLE 8

The procedure was conducted in the same manner as in Example 1 except that Nap—S—Leu—S—Phe—OMe, i.e., a compound represented by the formula [II]; $R^1$, an isobutyl group; $R^2$, a benzyl group; $R^3$, a methoxy group; $R^4$, a hydrogen atom; all of the absolute configurations thereof being S-isomers was used in place of the Nap—S—Val—S—Trp—OMe and that the stirring was continued at −20° C. for 4 hours in place of −40° C. for 3 hours, to give mandelonitrile. Yield: 93%. The product contained the R- and S-isomers at a ratio of 87.5:12.5.

EXAMPLE 9

The procedure was conducted in the same manner as in Example 1 except that the stirring was continued at −20° C. for 2.5 hours in place of −40° C. for 3 hours, to give mandelonitrile. Yield: 97%. The product contained the R- and S-isomers at a ratio of 91:9.

EXAMPLE 10

The procedure was conducted in the same manner as in Example 3 except that the stirring was continued at −20° C. for 4 hours in place of −40° C. for 4 hours, to give mandelonitrile. Yield: 91%. The product contained the R- and S-isomers at a ratio of 91:9.

EXAMPLE 11

The procedure was conducted in the same manner as in Example 2 except that Nap—S—Ile—S—Phe—OMe, i.e., a compound represented by the formula [II]; $R^1$: a sec. butyl group; $R^2$ a benzyl group; $R^3$, a methoxy group; $R^4$, a hydrogen atom; all of the absolute configurations thereof being S-isomers was used in place of the Nap—S—Val—S—Trp—OMe, to give mandelonitrile. Yield: 94%. The product contained the R- and S-isomers at a ratio of 86.5:13.5.

EXAMPLE 12

The procedure was conducted in the same manner as in Example 2 except that Nap—S—t—Leu—S—Phe—OMe, i.e., a compound represented by the formula [II]; $R^1$, a tert-butyl group; $R^2$, a benzyl group; $R^3$, a methoxy group; $R^4$, a hydrogen atom; all of the absolute configurations thereof being S-isomers was used in place of the Nap—S—val—S—Trp—OMe, that methylene chloride was used in place of the toluene, and that the stirring was continued at −20° C. for 4.5 hours in place of −20° C. for 2.5 hours, to give mandelonitrile. Yield: 74%. The product contained the R- and S-isomers at a ratio of 90:10.

EXAMPLE 13

The procedure was conducted in the same manner as in Example 2 except that Nap—S—Ala—S—Phe—OMe, i.e., a compound represented by the formula [II]; $R^1$, a methyl group; $R^2$, a benzyl group; $R^3$, a methoxy group; $R^4$, a hydrogen atom; all of the absolute configurations thereof being S-isomers was used in place of the Nap—S—Val—S—Trp—OMe and that the stirring was continued at −20° C. for 4 hours in place of −20° C. for 2.5 hours, to give mandelonitrile. Yield: 80%. The product contained the R- and S-isomers at a ratio of 79.5:20.5.

EXAMPLE 14

The procedure was conducted in the same manner as in Example 2 except that Nap—S—Phe—S—Phe—OMe, i.e., a compound represented by the formula [II]; $R^1$, a benzyl group; $R^2$, a benzyl group; $R^3$, a methoxy group; $R^4$, a hydrogen atom; all of the absolute configurations thereof being S-isomers was used in place of the Nap—S—Val—S—Trp—OMe and that the stirring was continued at −20° C. for 7.5 hours in place of −20° C. for 2.5 hours, to give mandelonitrile. Yield: 94%. The product contained the R- and S-isomers at a ratio of 83.5:16.5.

EXAMPLE 15

The procedure was conducted in the same manner as in Example 2 except that Nap—S—Val—S—Phe—NEt2, i.e., a compound represented by the formula [II]; $R^1$, an isopropyl group; $R^2$, a benzyl group; $R^3$, a diethylamino group; $R^4$, a hydrogen atom; all of the absolute configurations thereof being S-isomers was used in place of the Nap—S—Val—S—Trp—OMe and that the stirring was continued at −40° C. for 3 hours and further at −20° C. for 15 hours in place of −20° C. for 2.5 hours, to give mandelonitrile. Yield: 88%. The product contained the R- and S-isomers at a ratio of 90:10.

EXAMPLE 16

The procedure was conducted in the same manner as in Example 4 except that m-phenoxybenzaldehyde was used in place of the benzaldehyde, and that the stirring was continued at −40° C. for 11 hours and further at −20° C. for 12 hours in place of −40° C. for 4 hours, to give α-hydroxy-m-phenylacetonitrile. Yield: 85%. The product contained the R- and S-isomers at a ratio of 7:93.

EXAMPLE 17

The procedure was conducted in the same manner as in Example 3 except that cyclohexanecarboaldehyde was used in place of the benzaldehyde, and that the stirring was continued at −40° C. for 1.5 hours in place of −40° C. for 4 hours, to give α-hydroxy-cyclohexylacetonitrile. Yield: 99%. The product contained the R- and S-isomers at a ratio of 77:23.

In this connection, the ratio of the R- and S-isomers was determined by gas chromatography of the corresponding diastereomers, (+)-1-methoxy-1-phenyl-2,2,2-trifluoro-propionic acid ester derived from the product.

EXAMPLE 18

The procedure was conducted in the same manner as in Example 2 except that heptanal was used in place of the benzaldehyde, and that the stirring was continued at −40° C. for 1 hour in place of −20° C. for 2.5 hours, to give 2-hydroxyoctanenitrile. Yield: 99%. The product contained the R- and S-isomers at a ratio of 67:33.

In this connection, the ratio of the R- and S-isomers was determined by gas chromatography of the corresponding diastereomers, (+)-1-methoxy-1-phenyl-2,2,2-trifluoro-propionic acid ester derived from the product.

EXAMPLE 19

The procedure was conducted in the same manner as in Example 2 except that Nap—S—Val—S—Phe—OH, i.e., a compound represented by the formula [II]; $R^1$, an isopropyl group; $R^2$, a benzyl group; $R^3$, a hydroxy group; $R^4$, a hydrogen atom; all of the absolute configurations thereof being S-isomers, was used in place of the Nap—S—Val—S—Trp—OMe, and that the stirring was continued at −20° C. for 3 hours and further at 0° C. for 16 hours in place of −20° C. for 2.5 hours, to give mandelonitrile. Yield: 93%. The product contained the R- and S-isomers at a ratio of 71:29.

EXAMPLE 20

The procedure was conducted in the same manner as in Example 2 except that Nap—S—PhGly—S—Phe—OMe, i.e., a compound represented by the formula [II]; $R^1$, a phenyl group; $R^2$, a benzyl group; $R^3$, a methoxy group; $R^4$, a hydrogen atom; all of the absolute configurations thereof being S-isomers was used in place of Nap—S—Val—S—Trp—OMe, and that the stirring was continued at −20° C. for 20 hours in place of −20° C. for 2.5 hours, to give mandelonitrile. Yield: 62%. The product contained the R- and S-isomers at a ratio of 62.5:37.5.

Example 21

The procedure was conducted in the same manner as in Example 2 except that Nap—S—Val—S—PhGly—OMe, i.e., a compound represented by the formula [II]; $R^1$, an isopropyl group; $R^2$, a phenyl group; $R^3$, a methoxy group; $R^4$, a hydrogen atom; all of the absolute configurations thereof being S-isomers was used in place of the Nap—S'Val—S—Trp—OMe, and that the stirring was continued at −20° C. for 4 hours in place of −20° C. for 2.5 hours, to give mandelonitrile. Yield: 86%. The product contained the R- and S-isomers at a ratio of 62:38.

EXAMPLE 22

The procedure was conducted in the same manner as in Example 2 except that Nap—S—Val—S—Pro—OEt, i.e., a compound represented by the formula [II]; $R^1$, an isopropyl group; $R^2$ and $R^4$, a $CH_2CH_2CH_2$ group; $R^3$, an ethoxy group; all of the absolute configurations thereof being S-isomer was used in place of the Nap—S—Val—S—Trp—OMe and that the stirring was continued at −20° C. for 20 hours in place of −20° C. for 2.5 hours, to give mandelonitrile. Yield: 74%. The product contained the R- and S-isomers at a ratio of 66.5:33.5.

EXAMPLE 23

The procedure was conducted in the same manner as in Example 1 except that the stirring was continued at −60° C. for 16 hours in place of −40° C. for 3 hours, to give mandelonitrile. Yield: 83%. The product contained the R- and S-isomers at a ratio of 95:5.

EXAMPLE 24

The procedure was conducted in the same manner as in Example 3 except that titanium (IV) tetrabutoxide (0.05 mole) was used in place of the titanium (IV) tetraethoxide (0.05 mole) and that the stirring was continued at −20° C. for 4 hours in place of −40° C. for 4 hours, to give mandelonitrile. Yield: 84%. The product contained the R- and S-isomers at a ratio of 89:11.

EXAMPLE 25

The procedure was conducted in the same manner as in Example 1 except that Nap—S—Ile—S—Phe—OMe was used in place of the Nap—S—Val—S—Trp—OMe and that the stirring was continued at −40° C. for 4 hours in place of −40° C. for 3 hours, to give mandelonitrile. Yield: 85%. The product contained the R- and S-isomers at a ratio of 87.5:12.5.

EXAMPLE 26

The procedure was conducted in the same manner as in Example 1 except that Nap—S—Val—S—Val—OMe, i.e., a compound represented by the formula [II]; $R^1$, an isopropyl group; $R^2$, an isopropyl group; $R^3$, a methoxy group; $R^4$, a hydrogen atom; all of the absolute configurations thereof being S-isomers was used in place of the Nap—S—Val—S—Trp—OMe and that the stirring was continued at −40° C. for 4 hours in place of −40° C. for 3 hours, to give mandelonitrile. Yield: 64%. The product contained the R- and S-isomers at a ratio of 93.5:6.5.

EXAMPLE 27

The procedure was conducted in the same manner as in Example 1 except that Nap—S—Val—S—Leu—OMe, i.e., a compound represented by the formula [II]; R, an isopropyl group; $R^2$, an isobutyl group; $R^3$, a methoxy group; $R^4$, a hydrogen atom; all of the absolute configurations thereof being S-isomers was used in place of the Nap—S—Val—S—Trp—OMe and that the stirring was continued at −40° C. for 4 hours in place of −40° C. for 3 hours, to give mandelonitrile. Yield: 72%. The product contained the R- and S-isomers at a ratio of 79.5:20.5.

EXAMPLE 28

The procedure was conducted in the same manner as in Example 1 except that m-methoxybenzaldehyde was used in place of the benzyldehyde, and that the stirring was continued at −40° C. for 4 hours in place of −40° C. for 3 hours, to give α-hydroxy-(m-methoxyphenyl)-acetonitrile. Yield: 80%. The product contained the R- and S-isomers at a ratio of 92.5:7.5.

EXAMPLE 29

The procedure was conducted in the same manner as in Example 1 except that Sal—S—Val—S—Trp—OMe, i.e., a compound represented by the formula [I]; $R^1$, an isopropyl group; $R^2$, an indol-3-ylmethyl group; $R^3$, a methoxy group; $R^4$, a hydrogen atom; each of $R^5$, $R^6$, $R^7$ and $R^8$ is a hydrogen atom; all of the absolute configurations thereof being S-isomers was used in place of the Nap—S—Val—S—Trp—OMe, and that the stirring was continued at −40° C. for 4 hours in place of −40° C. for 3 hours to give manderonitrile. Yield 83%. The product contained the R- and S-isomers at a ratio of 89.5:10.5.

EXAMPLE 30

The procedure was conducted in the same manner as in Example 1 except that Nap'—S—Val—S—Trp—OMe, i.e., a compound represented by the formula [I]; $R^1$, an isopropyl group; $R^2$, an indol-3-ylmethyl group; $R^3$, a methoxy group; $R^4$, a hydrogen atom; each of $R^5$ and $R^6$ is a hydrogen atom; $R^7$ and $R^8$ are bonded together at their terminals to form CH=CH—CH=CH; all of the absolute configurations thereof being S-isomers was used in place of the Nap—S—Val—S—Trp—OMe, and that the stirring was continued at −40° C. for 2 hours in place of −40° C. for 3 hours to give manderonitrile. Yield 57%. The product contained the R- and S-isomers at a ratio of 87.5:12.5.

EXAMPLE 31

The procedure was conducted in the same manner as in Example 1 except that Sal'—S—Val—S—Phe—OMe, i.e., a compound represented by the formula [I]; $R^1$, an isopropyl group; $R^2$, a benzyl group; $R^3$, a methoxy group; $R^4$, a hydrogen atom; each of $R^5$, $R^6$ and $R^7$ is a hydrogen atom; R8 is a methoxy group; all of the absolute configurations thereof being S-isomers was used in place of the Nap—S—Val—S—Trp—OMe, and that the stirring was continued at −20° C. for 4 hours in place of −40° C. for 3 hours to give manderonitrile. Yield 68%. The product contained the R- and S-isomers at a ratio of 74:26.

EXAMPLE 32

The procedure was conducted in the same manner as in Example 1 except that Sal"—S—Val—S—Trp—OMe, i.e., a compound represented by the formula [I]; $R^1$, an isopropyl group; $R^2$, an indol-3-ylmethyl group; $R^3$, a methoxy group; $R^4$, a hydrogen atom; each of $R^5$ and $R^7$ is a hydrogen atom; each of $R^6$ and $R^8$ is a tert-butyl group; all of the absolute configurations thereof being S-isomers was used in place of the Nap—S—Val—S—Trp—OMe, and that the stirring was continued at −20° C. for 2.5 hours in place of −40° C. for 3 hours to give manderonitrile. Yield 70%. The product contained the R- and S-isomers at a ratio of 70:30.

The catalyst of the present invention is useful for preparation of optically active cyanohydrins with a high yield and a high optical purity by an addition of hydrogen chanide to aldehydes.

We claim:

1. A catalyst for asymmetric induction comprising the dipeptide derivative represented by the formula

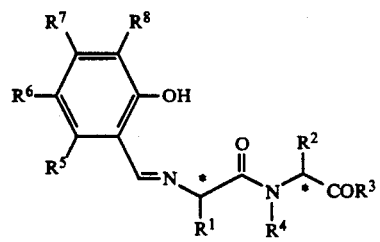

wherein $R^1$ represents an isopropyl group, an isobutyl group, a sec-butyl group, a tert-butyl group, a methyl group, a benzyl group or a phenyl group, $R^2$ represents a benzyl group, an indol-3-ylmethyl group, an isopropyl group, an isobutyl group or a phenyl group, $R^3$ represents a lower alkoxy group, a hydroxyl group or a mono- or di-lower alkylamino group, $R^4$ represents a hydrogen atom, or $R^2$ and $R^4$ are bonded together at their terminals to form a $CH_2CH_2CH_2$ group, $R^5,R^6,R^7$ and $R^8$ are the same or different, and each represents a hydrogen atom, a halogen atom, a lower alkyl group or a lower alkoxy group, or $R^5$ and $R^6,R^6$ and $R^7$, or $R^7$ and $R^8$ are bonded together at their terminals to form CH=CH—CH=CH or $OCH_2O$, and * denotes an absolute configuration of S or R, and a titanium (IV) alkoxide.

2. A catalyst for asymmetric induction comprising the dipeptide derivative represented by the formula

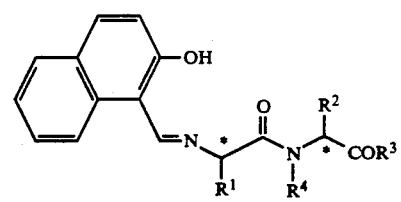

wherein $R^1$, $R^2$, $R^3$, $R^4$ and * are the same as those defined in claim 1, and a titanium (IV) alkoxide.

3. A catalyst according to claim 2, wherein $R^1$ represents an isopropyl, isobutyl, sec-butyl, tert-butyl, methyl or benzyl group, $R^2$ represents a benzyl or indol-3-ylmethyl group, $R^3$ represents a lower alkoxy, hydroxyl, or mono- or di-lower-alkylamino group, and $R^4$ represents a hydrogen atom.

4. A catalyst according to claim 1, wherein the titanium alkoxide is selected from the group consisting of titanium (IV) tetraethoxide, titanium (IV) tetraisopropoxide, titanium (IV) tetrapropoxide and titanium (IV) tetrabutoxide.

5. A catalyst according to claim 1, wherein the molar ratio of the titanium alkoxide and the dipeptide derivative ranges from 1:2 to 2:1.

6. A catalyst according to claim 1, wherein the molar ratio of the titanium alkoxide and the dipeptide derivative ranges from 1:1 to 2:1.

7. A catalyst according to claim 2, wherein the titanium alkoxide is selected from the group consisting of titanium (IV) tetraethoxide, titanium (IV) tetraisopropoxide, titanium (IV) tetrapropoxide and titanium (IV) tetrabutoxide.

8. A catalyst according to claim 2, wherein the molar ratio of the titanium alkoxide and the dipeptide derivative ranges from 1:2 to 2:1.

9. A catalyst according to claim 2, wherein the molar ratio of the titanium alkoxide and the dipeptide derivative ranges from 1:1 to 2:1.

10. A catalyst according to claim 3, wherein the titanium alkoxide is selected from the group consisting of titanium (IV) tetraethoxide, titanium (IV) tetraisopropoxide, titanium (IV) tetraethoxide and titanium (IV) tetrabutoxide.

11. A catalyst according to claim 3, wherein the molar ratio of the titanium alkoxide and the dipeptide derivative ranges from 1:2 to 2:1.

12. A catalyst according to claim 3, wherein the molar ratio of the titanium alkoxide and the dipeptide derivative ranges from 1:1 to 2:1.

* * * * *